(12) United States Patent
Meda et al.

(10) Patent No.: US 10,306,853 B1
(45) Date of Patent: Jun. 4, 2019

(54) RESISTANCE ALLELES IN SOYBEAN

(71) Applicant: Syngenta Participations AG, Basel (CH)

(72) Inventors: Anderson Rotter Meda, Londrina (BR); Becky Welsh Breitinger, Research Triangle Park, NC (US); Flavia Fernandes Carneiro, Uberlândia (BR); Andreomar Jose Kurek, Slater, IA (US)

(73) Assignee: Syngenta Participations AG, Basel (CH)

( * ) Notice: Subject to any disclaimer, the term of this patent is extended or adjusted under 35 U.S.C. 154(b) by 9 days.

(21) Appl. No.: 15/279,031

(22) Filed: Sep. 28, 2016

Related U.S. Application Data

(60) Provisional application No. 62/235,711, filed on Oct. 1, 2015.

(51) Int. Cl.
| | | |
|---|---|---|
| *A01H 5/10* | (2018.01) | |
| *A01H 1/02* | (2006.01) | |
| *C12Q 1/6895* | (2018.01) | |

(52) U.S. Cl.
CPC .............. *A01H 5/10* (2013.01); *A01H 1/02* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2014/0206032 A1 7/2014 Baley et al.

OTHER PUBLICATIONS

44363 Glycine max young leaves DNA genomic sequence with a NCBI/GenBank accession No. GF092901, published Dec. 2, 2008.*
Yamanaka et al., 2015, Euphytica 205: 311-324, published online Jan. 31, 2015.*
Choi et al., 2007, Genetics 176: 685-696.*
"Molecular mapping of soybean rust resistance in soybean accession PI561356 and SNP haplotype analysis of the Rpp1 region in diverse germplasm", Theor. Appl .Genet. 125(6), pp. 1339-1352, 2012.
"Molecular mapping of Asian soybean rust resistance in soybean landraces PI 594767A, PI 587905 and PI 416764", Plant Pathology, 2015 vol. 64, pp. 147-156.
"A High density integrated genetic linkage map of soybean and the development of a 1536 universal soy linkage panel for quantitative trait locus mapping", Crop Science, vol. 50, May-Jun. 2010.

* cited by examiner

*Primary Examiner* — Bratislav Stankovic
(74) *Attorney, Agent, or Firm* — R. Kody Jones

(57) ABSTRACT

The present invention relates to methods and compositions for identifying, selecting and/or producing a soybean plant or germplasm having resistance *Phakosora pachyrhizi*. A soybean plant, part thereof and/or germplasm that has been identified, selected and/or produced by any of the methods of the present invention is also provided. Also provided are single nucleotide polymorphisms (SNPs) associated with resistance to pathogens; and compositions including amplification primer pairs capable of initiating DNA polymerization by a DNA polymerase on soybean nucleic acid templates to generate soybean marker amplicons.

4 Claims, 1 Drawing Sheet

Specification includes a Sequence Listing.

Key rust tolerance traits: (1) lesion type and (2) rust severity

SEQUENCE LISTING

```
<160> NUMBER OF SEQ ID NOS: 35

<210> SEQ ID NO 1
<211> LENGTH: 459
<212> TYPE: DNA
<213> ORGANISM: Glycine max

<400> SEQUENCE: 1
ttttgatcca aaacaaagct gaaaagaaag gggacaggta tgaagcaatc ttcagcttct      60
actttggaga ctatggtcac atagcagtgc agggaccttg cctgacctat gaggacacat     120
atttggctgt gactggtggg tctggcatat ttgagggtgt taaaggtcaa gtgaagctgc     180
gtcagattgt gtatccttc aagattttgt acacatttta tctaagggt atcaaggatt       240 tgcctcagga gcttcttgtc aagactgttg agccaattcc atctgttgaa ccttcccctg     300
ctgctaaggc ccttgagccc aatgctacca ttgctggctt caccgactaa ttcatcaact     360
ttttttgtat ttgctttggc ctttgtagta gtatgattta agttactgaa taataataac     420
aagtgggrac tatgatgggt tttgtagtgg tggagtttc                            459

<210> SEQ ID NO 2
<211> LENGTH: 1204
<212> TYPE: DNA
<213> ORGANISM: Glycine max
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
```

```
<222> LOCATION: (893)..(893)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (971)..(971)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t
<220> FEATURE:
<221> NAME/KEY: misc_feature
<222> LOCATION: (1018)..(1018)
<223> OTHER INFORMATION: n is a, c, g, or t
<220> FEATURE:
<221> NAME/KEY: misc_feature
<222> LOCATION: (1024)..(1024)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1045)..(1045)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1093)..(1093)
<223> OTHER INFORMATION: n is a, c, g, or t

<400> SEQUENCE: 2
actctctagg aatatgattc ttccataata agtatatatg ataggaaatg atttttcatt      60
tttgacaaac taaatgttgc agtctctgtg cttgaaacaa tttaggttag gtaattaggt     120
tagcttttcc cataattgcc ataagaaaca ctgctccaaa cagtgttatc aattccgcct     180
tataaacatg ccattgcagg cttcccttca caaattgcct agggaggttg gcaaaaaacc     240
cactattcaa caacactggc tccaaagtag gaatccatgc tcaccacaac ataattgagt     300
tcagctttat cttttttatt gacagatccc cctccctctt gatattgatt tcgtttcctt     360
atgttgtgca tgattaatta atccatttt gcatttatgt taaatggagt ttgatggatt      420
ttgtattgat gttgtcttgc agcccaagag tgtcattttg tggctacagc attcctcatc     480
cttcagataa tcgtgttaat atcagagtcc agactacagg taagtaacta tgcagcatcg     540
tggtggatat aatgtgattg tgactttgat ttgcaaattt gtttccacaa tctagtctca     600
tgaatctatt tttgtattta aaatcacaag agtagtgtat acttagctac gaaattcgtg     660
ttttgttaga caatctcgaa tattttcttc acttactatt tgttacttt ggtagatatg       720 aagttgttaa taggagccaa acttttgtaa gccaactatt ctatcacagc attgtggtac     780 taaaaantt tnttatcatt gcatgrcatt ctctgttgaa ctaagaagtt ttcttatcag      840
agttcagata taaacacatt ataaggttta gagtttagac agtgcatcta tanataatta     900
agcagtcaaa cacattatan aaaattattt ttccttctata ataaaaaaac atagtaggat    960
gtactgatgt ngatcatcca caaataagtt ttacatcatg tatagcatga ctnttaanta   1020
```

```
atgnccatat gngtatttgc antangtttc ttgtatttttt atgctctaaa tttgtctatt    1080
tgcatnagta ttntgctgtt gaatgtgcga tttctgatgc atctgtaggc gatccatcac    1140
gcgaggtgtt aaaagatgca tgtcaagatc tgatgcttat gtgccaaaag ggtaggagca    1200
cttt                                                                 1204
```

<210> SEQ ID NO 3
<211> LENGTH: 1101
<212> TYPE: DNA
<213> ORGANISM: Glycine max
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (932)..(932)
<223> OTHER INFORMATION: n is a, c, g, or t

<400> SEQUENCE: 3

```
ttacaccaga atcatggcca ccaatcaaat acccctatca tcttattaca gaaaaggga       60 taagagaagg ggaaaaaaaa tctctagaaa ctgaagaatc aaggtttggt tcaaaaactg     120
tgcagttgcg ttagcatgtg aacaagctca tcactagaag gcctatctgc aggcatatca    180
gagaggcatg cagcagcaat cctaaccgcc attagcatct catcttcctc accttcttcc    240
cctaacatgc tcttntctag agcttcntgc gcctcgcccg cttgctgcaa gtgtctcagc    300
caacatccca aacttccccc actggctgct tctccaaaga atggatctgt aggatcctta    360
ccagttaaca aaacacctag tatcatgcca aaactaaaga tgtcactttt gtcagtgtac    420
ctgctgaaat tgccaaaaaa caccattcaa tctgaatacc atgaagctcc acatatacaa    480
gaatggaatg aagttaaaat aaacatctta ttggcaatac catcccata tatgcaatgc     540 catcaatcaa gcaatctttt attgttatta cttattgcta ttgatattga tgcatccaga    600
tatacaccac tgaaaaacta gaagtattcc aagttaaatt aggaaaaaaa acctttgtca    660
attattatta taatttagtt gtggtctcac tcaccaatct aggtttagta gtttgcagca    720
tgtgaactat aaactatatt attcatttgg accagactta gtgccaactg cctaaggtct    780
aaaacttgac atcaggaagt aatgggtagt tacaaaaaca aatagcaaag tctttattaa    840
ataataccaa attcaatcag caaatgatac aatgacaata cagattacag aatartaatt    900
tcgtttcaaa acaagagtct ttcattaggg tnctacaaag ggggcaaaaa accaatgagg    960
tgtggagctt ttgaaaaggt aacgaatcaa acaaattccc aatatcaacc acctaattag    1020
cctattggtg taaaaagtg aaagaacaga acagactaa gggaaaacac tagtgaatga     1080
gtatgattga aatttgtctt a                                             1101
```

<210> SEQ ID NO 4
<211> LENGTH: 620
<212> TYPE: DNA
<213> ORGANISM: Glycine max

<400> SEQUENCE: 4

```
ccactattgt ggccaaattc aaaacctcac agtcgcctcc ttttgaaagt caacaatatt       60
aaaaaataaa aaagcaacat actgtgatac taaaaagata ggaaactcaa ctgcaaagaa    120
tacaagttta tattattttta tttctaatga ttcttaaatg attgctatat atttgatgtg    180
```

```
ttttccttt  aagtagcaga  atacataaat  gggttaagaa  gtatcaaagt  ttggtttttc    240
ctttaagcat  cacttcactg  cttgaaacat  aaatgtatca  attaagaaat  aaactgaaar    300
aacagacctc  aattcgaatg  ccacagcctc  ttaaaaggac  tacatttgct  atgttcttcc    360
cttctgcagc  acgtttagca  ttcacaggat  gagaaaccaa  aattttgtt   atttccttgg    420 acagctcgtt  aacaacagca  gcagtgttcc  ttgcttcatg  agaatcatct  aaagcttctg    480 cttcaaaag   taagcggttg  tcctttaatg  ggtctgttcc  tgatatattt  ccactcagat    540
ttggtccttt  aacaaccact  ccacatctat  gttctgttgc  atacctaata  aaaaaatagc    600
tttttttttt  tttttttttt                                                   620
```

```
<210> SEQ ID NO 5
<211> LENGTH: 621
<212> TYPE: DNA
<213> ORGANISM: Glycine max
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t

<400> SEQUENCE: 5
```

```
caaacccgta  atatttaaag  ggtttaatat  ttttttttaat  tcttaatttt ttttaatttc     60 taaaacttt   tttagcattt  tttattctta  taattttctt  ctttaacagt  tttagttttt    120
tctataacat  taacaaatga  cttaacaagt  acaataacac  taactnacct  gtcgtgtata    180
cctatagtaa  ataaatatta  ttaattagcc  gcanctcaga  cgatccaaag  aaagaacagn    240
gaaaataaac  gaatacacaa  tattctggat  tttttgtcac  taatttgagt  tgttaggtca    300
wcaatgactt  ccagacatcc  ttaatgatct  tcatacaaga  taatatgaca  aatatgatgg    360
acttttgtcc  ctggcattag  tgtatcaaat  aatgtcgcca  ccagtaatgc  caacatagaa    420
aagggagata  aattagctga  aaaaagagag  taagagaagt  aaattattca  cgggctctca    480
aatgcccttg  attagagtca  taggaagcag  tatatcacct  tgtcaaaatg  ttttgattca    540
agccctaaag  gagctaaagc  tcaataatgg  tggccaaaga  aattatgtcc  atgtgctgca    600
gttttttttt  ttttttttt  t                                                 621
```

```
<210> SEQ ID NO 6
<211> LENGTH: 620
<212> TYPE: DNA
<213> ORGANISM: Glycine max
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t

<400> SEQUENCE: 6
```

```
tcacaatgcg aatagtgaaa caatcacaac tagaagttct cgcttcatcn tttttattcg    60
gagcatcgtt tcaaacacgt tagttttgca ttttgcaatt tttttttta aatcaatagg    120 ctctgttctg ctgaggaata cgtgtttaag gaataactac ccgagaacaa gcaaatccca   180
aacaacttgt attaacttct gaatatttta cgggatggtt tttttagatg tagattttga   240
gcattccttg agatgatata agattgtgtt ggtttaacca ataatggttg atataagtgr   300
tagttgtttg tgtctaggga tgagtataca tattcaggtc tactaatcgg tgggtggata   360
atttttctta agaccgtata aatatattga attttgagt tcaattcgtt aggtctacat    420
atctagntat atttaaaatg ttgatatatt ttagtctaat agattttagt ttaaaaaatg   480
aagtcaattt ttttttttaa ttttatataa ttttcacttt taaaaaaata tttatttata   540
aaaaatattt ttcaaattaa tagttgggntt tgtggactga ttcatttatt catgggtttt  600
tttttttttt tttttttttt                                               620

<210> SEQ ID NO 7
<211> LENGTH: 621
<212> TYPE: DNA
<213> ORGANISM: Glycine max
<220> FEATURE:
<221> NAME/KEY: misc_feature
<222> LOCATION: (394)..(394)
<223> OTHER INFORMATION: n is a, c, g, or t

<400> SEQUENCE: 7
gggagaatac ttccctggct tccttgcaat tggaactctt ggttcagaac gagtatctga   60
cccctcaaca acaccatcat ttcccatttc tgttgagagc ataactgaaa agaagatga   120 agtcactgag aatgatctga agctcatcaa tgatgagcta gagaaagttc taggagctga   180
aaccaaggat gatgttagca ttgactcctc aaggaggact agccatgtta gcactgggag   240
aagcagccat gtcagcactg ggagaagcag ccatgtcagc ataataacac tcagtggaaa   300
rccaatagaa ggcacagaac caaatggaaa tggtgctgca atttgtccac tccagggata   360
tctctttgga acagctattg aactgtctga aacnactgca gcagcagcaa agaaagaaca   420
taggacttcg ctcggggagc tgtttcagag aagcaaatca gctgaggaga atttcagcgc   480
aaaatgtgaa aggaggaca aaagagctga gaaggaagtg gacaagtctg ccatgaacct   540
gatgaaagaa aagctgaaga aaagaatgct ccatgcttat tctaagaatt ctacttcaat   600 atttttttt tttttttttt t                                              621

<210> SEQ ID NO 8
<211> LENGTH: 16
<212> TYPE: DNA
<213> ORGANISM: Artificial Sequence
<220> FEATURE:
<223> OTHER INFORMATION: Probe

<400> SEQUENCE: 8
agtggggact atgatg                                                   16

<210> SEQ ID NO 9
<211> LENGTH: 17
<212> TYPE: DNA
<213> ORGANISM: Artificial Sequence
<220> FEATURE:
<223> OTHER INFORMATION: Probe

<400> SEQUENCE: 9
agtgggaact atgatgg                                                  17
```

```
<210> SEQ ID NO 10
<211> LENGTH: 15
<212> TYPE: DNA
<213> ORGANISM: Artificial Sequence
<220> FEATURE:
<223> OTHER INFORMATION: Probe

<400> SEQUENCE: 10
attgcatgac attct                                                          15

<210> SEQ ID NO 11
<211> LENGTH: 15
<212> TYPE: DNA
<213> ORGANISM: Artificial Sequence
<220> FEATURE:
<223> OTHER INFORMATION: Probe

<400> SEQUENCE: 11
attgcatggc attct                                                          15

<210> SEQ ID NO 12
<211> LENGTH: 22
<212> TYPE: DNA
<213> ORGANISM: Artificial Sequence
<220> FEATURE:
<223> OTHER INFORMATION: Probe

<400> SEQUENCE: 12
ttgaaacgaa attattattc tg                                                  22

<210> SEQ ID NO 13
<211> LENGTH: 21
<212> TYPE: DNA
<213> ORGANISM: Artificial Sequence
<220> FEATURE:
<223> OTHER INFORMATION: Probe

<400> SEQUENCE: 13
tgttttgaaa cgaaattact a                                                   21

<210> SEQ ID NO 14
<211> LENGTH: 19
<212> TYPE: DNA
<213> ORGANISM: Artificial Sequence
<220> FEATURE:
<223> OTHER INFORMATION: Probe

<400> SEQUENCE: 14
cgaattgagg tctgttctt                                                      19

<210> SEQ ID NO 15
<211> LENGTH: 20
<212> TYPE: DNA
<213> ORGANISM: Artificial Sequence
<220> FEATURE:
<223> OTHER INFORMATION: Probe

<400> SEQUENCE: 15
tcgaattgag gtctgttttt                                                     20

<210> SEQ ID NO 16
<211> LENGTH: 18
<212> TYPE: DNA
<213> ORGANISM: Artificial Sequence
<220> FEATURE:
```

```
<223> OTHER INFORMATION: Probe

<400> SEQUENCE: 16
tgagttgtta ggtcaaca                                                 18

<210> SEQ ID NO 17
<211> LENGTH: 18
<212> TYPE: DNA
<213> ORGANISM: Artificial Sequence
<220> FEATURE:
<223> OTHER INFORMATION: Probe

<400> SEQUENCE: 17
tgagttgtta ggtcatca                                                 18

<210> SEQ ID NO 18
<211> LENGTH: 16
<212> TYPE: DNA
<213> ORGANISM: Artificial Sequence
<220> FEATURE:
<223> OTHER INFORMATION: Probe

<400> SEQUENCE: 18
cacaaacaac taccac                                                   16

<210> SEQ ID NO 19
<211> LENGTH: 19
<212> TYPE: DNA
<213> ORGANISM: Artificial Sequence
<220> FEATURE:
<223> OTHER INFORMATION: Probe

<400> SEQUENCE: 19
tagacacaaa caactatca                                                19

<210> SEQ ID NO 20
<211> LENGTH: 16
<212> TYPE: DNA
<213> ORGANISM: Artificial Sequence
<220> FEATURE:
<223> OTHER INFORMATION: Probe

<400> SEQUENCE: 20
cactcagtgg aaaacc                                                   16

<210> SEQ ID NO 21
<211> LENGTH: 15
<212> TYPE: DNA
<213> ORGANISM: Artificial Sequence
<220> FEATURE:
<223> OTHER INFORMATION: Probe

<400> SEQUENCE: 21
ctcagtggaa agcca                                                    15

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
aggatttgcc tcaggagctt                                               20
```

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gaaactccac cactacaaaa cc							22

<210> SEQ ID NO 24
<211> LENGTH: 38
<212> TYPE: DNA
<213> ORGANISM: Artificial Sequence
<220> FEATURE:
<223> OTHER INFORMATION: Primer

<400> SEQUENCE: 24
ctctaaacct tataatgtgt ttatatctga actctgat					38

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
aagccaacta ttctatcaca gcattgt						27

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
caaaagctcc acacctcatt gg							22

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
ttgacatcag gaagtaatgg gtagt						25

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28 tcctttttaag aggctgtggc at						22

<210> SEQ ID NO 29
<211> LENGTH: 25
<212> TYPE: DNA
<213> ORGANISM: Artificial Sequence
<220> FEATURE:
<223> OTHER INFORMATION: Primer

```
<400> SEQUENCE: 29
gcatcacttc actgcttgaa acata                                         25

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
ctcagacgat ccaaagaaag aaca                                          24

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
ggtggcgaca ttatttgata cac                                           23

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
cccaccgatt agtagacctg aa                                            22

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
ccgagaacaa gcaaatccca aac                                           23

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
tcagcactgg gagaagca                                                 18

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
gtggacaaat tgcagcacca tt                                            22
```

RESISTANCE ALLELES IN SOYBEAN

RELATED APPLICATION INFORMATION

This Application claims the benefit of U.S. Provisional Application No. 62/235,711, filed 1 Oct. 2015, the contents of which are incorporated herein by reference.

STATEMENT REGARDING ELECTRONIC FILING OF A SEQUENCE LISTING

A Sequence Listing in ASCII text format, submitted under 37 C.F.R. § 1.821, entitled "80753 SEQ LISTING_ST25.txt", 14.3 kilobytes in size, generated on Sep. 1, 2015 and filed via EFS-Web, is provided in lieu of a paper copy. This Sequence Listing is hereby incorporated by reference into the specification for its disclosures.

FIELD OF THE INVENTION

The present invention relates to compositions and methods for identifying, selecting and/or producing soybean plants having tolerance to Asian soy rust

BACKGROUND

Soybean (*Glycine max* L. Merr) is a major cash crop and investment commodity in North America and elsewhere. Soybean oil is one of the most widely used edible oils, and soybeans are used worldwide both in animal feed and in human food production. Asian soy rust (ASR) in soybeans is a widespread problem in many parts of the world particularly in Brazil.

Different varieties of soybean vary in their sensitivity or tolerance to ASR. Therefore, one of the most effective control measures is planting Asian soy rust tolerant soybean varieties, and thus varietal selection is important for the management of ASR. However, currently, determining whether a soybean cultivar might have tolerance to ASR typically involves testing each cultivar in the field or greenhouse under conditions that typically produce ASR symptoms. Thus, the present invention overcomes the shortcomings in the art by providing molecular markers associated with tolerance to ASR, thereby allowing the characterization of soybean cultivars for ASR by molecular analysis rather than phenotypic analysis.

SUMMARY OF THE INVENTION

Description of the Figures

FIG. 1: is a photograph showing Rpplb's effect against rust under field conditions

DEFINITIONS

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker (e.g., SNP, QTL, haplotype) can mean one marker or a plurality of markers (e.g., 2, 3, 4, 5, 6, and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.—In some embodiments of this invention, the phrase "desired allele," "target allele" or "allele of interest" refers to an allele(s) that is associated with tolerance to ASR in a soybean plant relative to a control soybean plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with an ASR tolerance allele" refers to a marker whose presence or absence can be used to predict whether a plant will display tolerance to ASR.

As used herein, the term "ASR" or "Asian soy rust tolerance" refers to a plant's ability to endure and/or thrive despite being exposed to growth conditions in which ASR are low as compared to one or more control plants (e.g., a plant lacking a marker associated with ASR).

Thus, "tolerance" in a soybean plant to ASR conditions is an indication that the soybean plant is less affected by the ASR conditions with respect to yield, survivability and/or other relevant agronomic measures, compared to a less tolerant, more "susceptible" plant. Tolerance is a relative term, indicating that a "tolerant" soybean plant survives and/or produces a better yield in ASR growth conditions when compared to a different (less tolerant) soybean plant (e.g., a different soybean strain or variety) grown in similar conditions ASR. That is, under ASR growth conditions a tolerant plant can have a greater survival rate and/or yield, as compared to a soybean plant that is susceptible or intolerant to these ASR growth conditions. Asian soy rust "tolerance" sometimes can be used interchangeably with Asian soy rust "resistance". Asian soy rust intolerant soybean varieties and cultivars are well known in the art.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with ASR tolerance may be introgressed from a donor into a recurrent parent that is ASR. The resulting offspring could then be backcrossed one or more times and selected until the progeny possess the genetic marker(s) associated with ASR in the recurrent parent background.

As used herein, the term "linkage" refers to the degree with which one marker locus is associated with another marker locus or some other. The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., ASR. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, Theor. Appl. Genet. 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., Nature Reviews Genetics 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, Trends in Genetics 9:275 (1993)), an amplified fragment length polymorphism (AFLP) (Vos et al., Nucleic Acids Res. 23:4407 (1995)), a single nucleotide polymorphism (SNP) (Brookes, Gene 234: 177 (1993)), a sequence-characterized amplified region (SCAR) (Paran and Michelmore, Theor. Appl. Genet. 85:985 (1993)), a sequence-tagged site (STS) (Onozaki et al., Euphytica 138:255 (2004)), a single-stranded conformation polymorphism (SSCP) (Orita et al., Proc. Natl. Acad. Sci. USA 86:2766 (1989)), an inter-simple sequence repeat (ISSR) (Blair et al., Theor. Appl. Genet. 98:780 (1999)), an inter-retrotransposon amplified polymorphism (IRAP), a retrotransposon-microsatellite amplified polymorphism (REMAP) (Kalendar et al., Theor. Appl. Genet. 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase Internet resource (soybase.org). In some embodiments, a genetic marker of this invention is an SNP allele, a SNP allele located in a chromosome interval and/or a haplotype (combination of SNP alleles) each of which is associated with Asian soy rust tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Tables 1-3)

Accordingly, in some embodiments of this invention, a marker is detected by amplifying a Glycine sp. nucleic acid with two oligonucleotide primers by, for example, the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Non-limiting examples of probes of this invention include SEQ ID NOs:19-54 and 137-300.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition,* Cold Spring Harbor Laboratory Press, Cold Spring Harbor, N.Y., United States of America. Generally, lower salt concentration and higher temperature hybridization and/or washes increase the stringency of hybridization conditions.

As used herein, the term "probe" refers to a single-stranded oligonucleotide sequence that will form a hydrogen-bonded duplex with a complementary sequence in a target nucleic acid sequence analyte or its cDNA derivative.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997)

*Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST®X version 2.0 for translated nucleotide sequences and BLAST®N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST®) programs which are publicly available from National Center Biotechnology Information (NCBI) at the National Library of Medicine, National Institute of Health, Bethesda, Md. 20894; see BLAS®T Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence BLAST®X can be used to determine sequence identity; and for polynucleotide sequence BLAST®N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "soybean" refers to a plant, and any part thereof, of the genus *Glycine* including, but not limited to *Glycine max*.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny", "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

As used herein, the term "reference sequence" refers to a defined nucleotide sequence used as a basis for nucleotide sequence comparison. The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

Genetic Mapping

Genetic loci correlating with particular phenotypes, such as ASR, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with ASR in soybean. Detection of these markers and/or other linked markers can be used to identify, select and/or produce soybean plants having ASR and/or to eliminate soybean plants from breeding programs or from planting that do not have ASR.

Markers Associated with ASR

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) Methods in Plant Molecular Biology and Biotechnology, CRC Press, Boca Raton, Fla., United States of America; Zietkiewicz et al. (1994) Genomics 20:176-183.

In one embodiment of the invention, it is contemplated that one may use gene editing technologies (e.g. Talen, Meganucleases, CRISPR, etc.) to introduce a favorable allele introduction for ASR resistance into a soybean germplasm not comprising said favorable allele wherein the favorable allele is on chromosome 18 and within 20 cM, 10 cM, 5 cM or less from a chromosomal interval comprising physical positions 58,722,971-60,910,083 or any favorable allele or favorable haplotype as described in Tables 1 or 2.

Table 1 provides information about the ASR associated markers presented including the physical location of the marker on the respective soybean chromosome, and the target allele that is associated with ASR. Table 2 gives the names of the associated markers (SNPs) of this invention, the specific associated ASR trait or traits, the physical genetic locations of each marker on the respective soybean chromosome or linkage group, and the target allele that is associated with ASR.

Markers of the present invention are described herein with respect to the positions of marker loci in the 8X public build of the Williams82 soybean genome at the SoyBase internet resource (soybase.org/SequenceIntro.php) or USDA at (bf-gl.anri.barc.usda.gov/egi-bin/soybean/Linkage.pl). See Table 1 below.

TABLE 1

The respective soybean chromosome or linkage group of physical and genetic positions including the sequence identifiers for the DNA fragments comprising the SNPs or indels and two probes sequences with tagged SNP allele for each assay for the genetic markers presented.

| Assay Name | Linkage Group (chromosome #) | Physical position SNP in Willams 82 genome | SEQ ID NO for fragment comprising marker | Favorable allele (respective SNP position in fragment of column 5) | Probe 1 SEQ ID NO (detected nucleotide) | Probe 2 SEQ ID NO (detected nucleotide) | Primer SEQ ID NO's |
|---|---|---|---|---|---|---|---|
| SY0707A | G (18) | 60469365 | 1 | A (428) | 8 (G) | 9 (A) | 22, 23 |
| SY0708A | G (18) | 60488141 | 2 | A (806) | 10 (A) | 11 (G) | 24, 25 |
| SY0714DQ | G (18) | 60577761 | 3 | A (895) | 12 (A) | 13 (G) | 26, 27 |
| SY3765 | G (18) | 60320484 | 4 | G (300) | 14 (G) | 15 (A) | 28, 29 |
| SY3771 | G (18) | 60634861 | 5 | T (301) | 16 (A) | 17 (T) | 30, 31 |
| SY3776 | G (18) | 60780364 | 6 | A (300) | 18 (G) | 19 (A) | 32, 33 |
| SY3777 | G (18) | 60802607 | 7 | A (301) | 20 (A) | 21 (G) | 34, 35 |

TABLE 2

Shows respective plant introduction lines (rust tolerant and susceptible) and respective haplotypes for each. The Table further shows lesion types (TAN or RB1, see FIG. 1)

| PI # | Lesion type in Brazil | Locus/ haplotype | SNP assay | | | | | | |
|---|---|---|---|---|---|---|---|---|---|
| | | | SY3765 | SY0707A | SY0708A | SY0714DQ | SY3771 | SY3776 | SY3777 |
| | | | Physical Map position | | | | | | |
| | | | 60.320.484 | 60.469.365 | 60.488.141 | 60.577.761 | 60.634.861 | 60.780.364 | 60.802.607 |
| PI 200492 | TAN | Rpp1-hap1 | G | A | A | A | T | A | G |
| PI 368038 | TAN | Rpp1-hap1 | G | A | A | A | T | A | G |
| PI 368039 | TAN | Rpp1-hap1 | G | A | A | A | T | A | G |
| PI 547875 | TAN | Rpp1-hap1 | G | A | A | A | T | A | G |
| PI 594754 | RB1 | Rpp1-hap2 | A | G | A | A | T | G | G |
| PI 594760B | RB1 | Rpp1-hap2 | A | G | A | A | T | G | G |
| PI 594767A | RB1 | Rpp1-hap2 | A | G | A | A | T | G | G |
| PI 587880A | RB1 | Rpp1b | G | A | A | A | A | G | A |
| PI 587905 | RB1 | Rpp1b | G | A | A | A | A | G | A |
| PI 561356 | RB1 | Rpp1b | G | A | A | A | A | G | A |
| PI 594538A | RB1 | Rpp1b | G | A | A | A | A | G | A |
| BA821791 | TAN | susceptible | A | G | G | G | T | A | G |
| BENNING | TAN | susceptible | A | G | G | G | A | A | G |

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A method of producing an Asian Soybean Rust (ASR) tolerant soybean plant or part thereof, the method comprising the steps of:

a. isolating a nucleic acid from a first soybean plant or part thereof;

b. detecting in said nucleic acid, the presence of a marker associated with ASR tolerance in a soybean plant, wherein said marker is located within a chromosomal interval on soybean chromosome 18 corresponding to physical positions 58,722,971-60,802,607 and further wherein the chromosomal interval comprises an allele associated with ASR tolerance, wherein said allele corresponds to an A at position 806 of SEQ ID NO: 2;

c. crossing the first soybean plant having in its genome the marker associated with ASR from b) with a second soybean plant not comprising said marker; and d. producing a progeny soybean plant from the cross of c) wherein said progeny plant comprises in its genome the marker detected in b).

2. The method of claim 1, wherein the chromosome interval is derived from any of PI587880A, PI587905, PI561356, PI594538A, or a progeny thereof.

3. The method of claim 1, wherein the marker is a haplotype comprising an A at position 428 of SEQ ID NO: 1; an A at position 806 of SEQ ID NO: 2; an A at position 895 of SEQ ID NO: 3; a G at position 300 of SEQ ID NO: 4; a T at position 301 of SEQ ID NO: 5; an A at position 300 of SEQ ID NO: 6; and an A at position 301 of SEQ ID NO: 7.

4. The method of claim 1, wherein the chromosomal interval further comprises an allele associated with ASR tolerance that corresponds to: an A at position 428 of SEQ ID NO:1; an A at position 895 of SEQ ID NO:3; a G at position 300 of SEQ ID NO:4; a T at position 301 of SEQ ID NO:5; an A at position 300 of SEQ ID NO:6; an A at position 301 of SEQ ID NO:7; or any combination thereof.

* * * * *